(12) United States Patent
Gleich et al.

(10) Patent No.: US 12,419,535 B2
(45) Date of Patent: Sep. 23, 2025

(54) PASSIVE WIRELESS COIL-BASED MARKERS AND TRACKING SYSTEM

(71) Applicant: KONINKLIJKE PHILIPS N.V., Eindhoven (NL)

(72) Inventors: Bernhard Gleich, Hamburg (DE); Jürgen Erwin Rahmer, Hamburg (DE); Ingo Schmale, Hamburg (DE); Tim Nielsen, Hamburg (DE); Richard Moessel, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 246 days.

(21) Appl. No.: 18/267,807

(22) PCT Filed: Dec. 16, 2021

(86) PCT No.: PCT/EP2021/086146
§ 371 (c)(1),
(2) Date: Jun. 16, 2023

(87) PCT Pub. No.: WO2022/129310
PCT Pub. Date: Jun. 23, 2022

(65) Prior Publication Data
US 2024/0049978 A1 Feb. 15, 2024

(30) Foreign Application Priority Data
Dec. 18, 2020 (EP) .................................. 20215374

(51) Int. Cl.
*A61B 5/06* (2006.01)
(52) U.S. Cl.
CPC .............. *A61B 5/062* (2013.01); *A61B 5/064* (2013.01)

(58) Field of Classification Search
CPC ................................ A61B 5/062; A61B 5/064
See application file for complete search history.

(56) References Cited

U.S. PATENT DOCUMENTS

| 5,057,095 A | 10/1991 | Fabian | |
| 2003/0192557 A1* | 10/2003 | Krag | A61B 34/74 128/898 |

(Continued)

FOREIGN PATENT DOCUMENTS

WO    WO20190243098 A1    12/2019

OTHER PUBLICATIONS

PCT International Search Report, International application No. PCT/EP2021/086146, Apr. 7, 2022.

*Primary Examiner* — Gerald Johnson

(57) ABSTRACT

A wireless passive marker device (1) to be tracked and a respective tracking system (3) are provided which make use of a sensing unit (10) comprising a resonator element (11) with piezoelectric properties and a coil element (13), whereby an externally applied excitation field having a particular frequency is applied to act on the sensing unit (10) and wherein the sensing unit (10) responds to the externally applied excitation field by the resonator element (11) performing persisting mechanical oscillations in resonant mode, the persisting mechanical oscillations resulting in a piezoelectric voltage causing the coil element (13) to generate a magnetic field that may then be detected by the tracking system (3) and used for determining the position of the marker device (1) and/or sensing a physical property in the surrounding environment of the marker device (1).

15 Claims, 3 Drawing Sheets

(56) References Cited

U.S. PATENT DOCUMENTS

| | | | |
|---|---|---|---|
| 2004/0138555 A1* | 7/2004 | Krag | A61B 17/32053 128/899 |
| 2007/0236213 A1 | 10/2007 | Paden | |
| 2007/0265491 A1* | 11/2007 | Krag | A61B 17/32053 600/37 |
| 2013/0096825 A1 | 4/2013 | Mohanty | |

* cited by examiner

PASSIVE WIRELESS COIL-BASED MARKERS AND TRACKING SYSTEM

FIELD OF THE INVENTION

The invention relates to a passive marker device to be tracked, a tracking system for tracking such a marker device, a method for tracking a marker device, and a computer program for controlling the tracking system.

BACKGROUND OF THE INVENTION

For certain medical procedures it is beneficial to track a medical device which is used procedure in the procedure, such as the medical interventional device, during said procedure. This tracking should hereby be as accurate as possible.

Further, it may be beneficial, during these procedures, to be able to sense certain physical parameters in the surrounding environment of the device, in particular the medical device. In this case also, the sensing should be very sensitive to changes.

In case of very small devices, it may be challenging to provide a measure that allows tracking of the devices and/or sensing of physical parameters with high accuracy.

For this purpose, a system for miniature markers and sensors has recently been described in WO2019243098, which is based on the usage of so-called micro-magnetic oscillators (MMOs). In these systems, the initiation of a mechanical oscillation in the micro-magnetic oscillators in response to a magnetic or electromagnetic excitation field is used for tracking the marker devices comprising these micro-magnetic oscillators and, therefore, the devices these marker devices are attached to.

Hereby, the mechanical oscillation of the micro-magnetic oscillators results in an oscillating magnetic field that may be detected by a respective tracking array, such as a coil array comprising a number of coils. Depending on the distance and orientation of the magnetic field to the individual coils in the coil array, the response induced in each of the coils will be different. That is, for each of the coils, a value is provided, meaning 16 values are provided for example in a 4×4 coil array. In order to perform tracking, i.e. determine the position and orientation of the marker device and, hence, the device the marker device is attached to, 6 values are needed. Thus, the responses detected by the 16 coils are sufficient to determine position and orientation of the marker device in the excitation field.

The benefit of these micro-magnetic oscillators resides in the fact that they have shown to have a high quality factor and, thus, exhibit only little damping. As such, respective readout systems may be relatively slow, allowing to use relatively simple and inexpensive readout systems for detecting the mechanical oscillations and, thereby, the marker devices.

In modalities directed to tracking and/or sensing, the field-of-view achieved is limited by the available signal-to-noise ratio. For micro-magnetic oscillators, this signal-to-noise ratio scales with the square of the linear dimensions of the devices. Accordingly, these devices become less and less beneficial with increasing spaces available.

By contrast, well-known magnetic coil resonators, such as LC resonators, have a signal-to-noise ratio that scales with a fifth power of the linear dimensions. This means that, at larger sizes, these magnetic coil resonators may be superior to the micro-magnetic oscillators. The drawback of this approach, however, resides in the fact that the quality factors of these magnetic coil resonators are very low, leading to these kinds of resonators exhibiting a relatively strong damping. Therefore, in order to be accurate, magnetic coil resonators need to be read out fast. This means that fast and, thus, complex and costly, readout systems are needed.

Further, due to the low quality factor, the frequency resolution of the magnetic coil resonators is also low. This means that magnetic coil resonators only have a limited sensitivity to physical parameter changes. They also do not allow to perform gradient based position tracking.

SUMMARY OF THE INVENTION

As discussed herein above, the drawback of magnetic coil resonators mainly resides in their low quality factor which means that very complex read-out systems are needed to obtain accurate results. This is the case since, in typical readout systems, a switching has to be performed between the provision of the excitation field and the reception of the response field, since the excitation field is typically much larger than the response field. Thus, for the time the switching takes place, the tracking array may not be operational.

For the cases where the quality factor is low and the damping of the resonator circuit is therefore strong, a very fast switching is required in order to not deteriorate the results. In order to obtain sufficiently fast switching, expensive electronic switches are needed that are used such as to perform switching as quickly as possible, while at the same time ensuring that the tracking array is not damaged. This makes the process somewhat complex and prone to errors. It also bears a higher risk to damage the tracking array.

By contrast, for cases where the quality factor is high and the damping is low, there is no need for a fast switching. Thus, the use of expensive electronics is not necessary. Further, since the switching can be performed in a somewhat slower manner, the risk of damaging the tracking array is reduced.

In view of the above, it is an object of some embodiments of the present invention to provide a marker device, in particular a marker device configured to be attached to a device, in particular a medical device, that allows overcoming the above-described shortcomings.

More particularly, it is an object of some of the embodiments of the invention to improve the tracking and sensing methods known in the prior art.

Further, it is an object of some of the embodiments of the invention to provide a marker device that allows for tracking of a device and sensing of physical parameter changes in a larger variety of different situations and under different conditions.

Even more particularly, it is an object of some embodiments of the invention to provide a marker device to be tracked and a corresponding tracking system for tracking the same, which may be used for both, tracking and sensing physical parameter changes, which exhibits high accuracy using a relatively simple readout system.

This object is achieved, in a first aspect, by a marker device to be tracked, wherein the marker device comprises a sensing unit comprising a resonator element having piezoelectric properties and a coil element, wherein the coil element may be configured to transduce an external magnetic or electromagnetic excitation field into an output voltage to be provided to the resonator element and the resonator element may be configured to transduce the output voltage into respective mechanical oscillations in a resonant mode and to provide a piezoelectric voltage to the coil element. The coil element may then be configured to transduce the piezoelectric voltage into a magnetic field to be detected by a tracking array in the tracking system.

That is, the object is solved by an approach in which the marker device comprises a sensing unit in which a magnetic coil resonator, in terms of the coil element, is combined with an energy-storing oscillator, in terms of the resonator element having piezoelectric properties. More particularly, the object is solved by using an externally applied magnetic or electromagnetic excitation field to cause mechanical oscillations at the resonance frequency of the resonator element. Hereby, the oscillation is persistent due to the high quality factor of the circuit. This quality factor may particularly be a quality factor having a value above $10^3$ or even higher.

In this context, the term marker device may particularly be understood as referring to a device that may be attached to a device to be tracked, in particular a medical device, in order to track said medical device. The marker device may hereby be used to determine the position of the medical device to which it is attached.

The term sensing unit may particularly be understood as defining a unit that allows for tracing the marker device by means of a tracking array and/or, in some embodiments, for sensing a physical parameter using the marker device. In the sensing unit, a coil element, i.e. a magnetic coil resonator, such as an LC resonator, and a piezoelectric resonator element are provided.

Hereby, the coil element and the resonator element may particularly be electrically connected to one another. The coil element may particularly comprise or be made of a copper. The coil element may, alternatively or additionally, comprise or be made of silver. In some embodiments, in particular embodiments where the marker device is supposed to be transparent to radiation, the coil element may comprise or be made of aluminum. In some embodiments, in particular embodiments where the marker device is supposed to be opaque to radiation, gold may be chosen for the windings to serve dual purpose.

Further, the term resonator element may, in this context, be understood as corresponding to an element that is connected to the coil element in order to respond to the coil element's voltage output in response to an externally applied magnetic or electromagnetic field by respectively deforming and, thus, starting to perform mechanical oscillations. The resonator element may particularly comprise a crystal, such as a quartz crystal. The resonator element may be made of a different material, such as certain ceramics or the like.

The mechanical oscillations of the resonator device may particularly be provided in resonant mode. This is to be understood as meaning that the resonator device may, in response to the output voltage applied to it, start oscillating at or near to is resonance frequency. In some embodiments, this is achieved by having the externally applied magnetic or electromagnetic field provided with the right frequency components to lead to an output voltage of the coil element that achieves such resonant mechanical oscillations. Due to the resonator element oscillating at its resonance frequency, it acts as an energy storage even in cases where no output voltage is applied anymore. This reduces the damping of the resonant circuit formed by the coil element and the resonator element.

The resonator element may be electrically connected to the coil element via respective contacts.

Further, the resonator element may have piezoelectric properties. In this context, the term piezoelectric properties shall be understood within the conventional meaning, i.e. as describing a material which deforms in response to an electrical voltage being applied thereto and which, in response to the mechanical stress exerted by the deformation accumulates and electric charge that may be output in terms of a piezoelectric voltage. The accumulation of electric charge may hereby happen in a reversible manner, i.e. changes in mechanical stress from a first to a second state may lead to the electric charge being accumulated and changes from the second to the first state in mechanical stress will result in the material having the same (electric) properties as before again.

The term coil element may particularly refer to an element comprising and/or corresponding to a magnetic coil arrangement having a particular number of windings. The coil element may be an off-the-shelf magnetic coil having an appropriate number of windings, an appropriate size and an appropriate distance between the windings. The amount and size of and distance between the windings may hereby particularly be determined on the basis of the desired magnetic properties of the coil element. In some embodiments, in particular in embodiments, where space needs to be saved, the resonator element may be provided inside the coil element and may be electrically connected to the contacts of the coil element. Alternatively, the resonator element may be provided at some distance away from the coil element while still being electrically connected thereto via respective contacts. The coil element may particularly be provided by winding a coil around the resonator element, whereby the coil is wound in a manner such that it does not touch the resonator element.

The coil element may be arranged at a distance from the resonator element. The resonator element and the coil element may, for this purpose, be connected via a respective connection portion. In some embodiments, in particular embodiments where space has to be saved, the distance may be achieved by providing the windings around the resonator element such that there is a space between the windings of the coil element and the resonator element. The dimensions of this space should hereby be chosen appropriately according to the dimensioning of the marker device. Hereby, it should be noted that the windings of the coil element become more efficient when they are further away from a rotational axis of the coil element. The arrangement between the resonator element and the coil element may therefore be such that the resonator element may be provided in the coil element and extends along its axis.

According to the claimed concept, an externally applied magnetic or electromagnetic excitation field may be provided. This externally applied magnetic or electromagnetic excitation field may have at least one frequency component that allows the coil element to generate and output an output voltage that allows to excite the resonator element to perform mechanical oscillations in resonant mode.

For this purpose, the externally applied magnetic or electromagnetic field may act on the coil element. In response to this, the coil element may transduce the externally applied magnetic or electromagnetic field into a respective output voltage.

As indicated, the coil element is electrically connected to the resonator element. Accordingly, the output voltage provided by the coil element is output through the input/output terminals of the resonator element to the resonator element via the electrical connection. The output voltage is thus fed to the respective input/output terminals of the resonator element.

The resonator element, having piezoelectric properties, is then deformed by the voltage applied to it from the coil element. Accordingly, the resonator element starts performing mechanical oscillations. Hereby, the deformation is dependent on the frequency components of the applied output voltage, which, in turn, is dependent on the frequency components of the externally applied magnetic or electromagnetic excitation field.

As stated, the frequency components may be provided to be within a resonance frequency of the resonator element. In this case, the mechanical oscillations are excited in the resonant mode. That is, the resonator element oscillates close to its resonant frequency. The respective oscillations may then persist for some time, independent of whether or not voltage is provided from the coil.

The deforming of the resonator element having the piezoelectric properties, in turn, causes a piezoelectric voltage to be generated and output through its input/output terminals. This piezoelectric voltage is then provided, via the input/output terminals, to the coil element. This causes a current through the coil element. In response to this, the coil element produces a magnetic field which may then be picked up as an oscillation response by the tracking system.

For this purpose, the tracking system may comprise a respective tracking array, comprising a plurality of oscillation response detection units that are configured to detect the magnetic field. These oscillation response detection units may hereby be arranged in a particular geometrical arrangement, such as a 4×4 array. The oscillation response detection units may particularly comprise a plurality of coils which may be arranged in a 4×4 coil array having 4×4 flat coils on a plane arranged in a chessboard structure.

Hereby, the magnetic field that is picked up by each one of the individual oscillation response detection units, in particular the coils, is dependent on the distance and orientation of the marker device relative to the respective oscillation response detection unit. This may give up to 16 different measurement values for the magnetic field.

The thus generated response signal may then be provided to a processor acting as a position determination unit. The position determination unit may particularly be configured to model the response signals that would be generated for different positions and orientations of the marker device and compare it to the response signal received. The best match is then considered the position which is described in terms of amplitude, three coordinates and two angles.

The position may be determined by a gradient-based position encoding. In these embodiments, an externally applied magnetic field, which may correspond to the excitation field or may, alternatively, be provided in addition to the excitation field in terms of a separate saturating magnetic field is provided to act on the marker device, whereby the magnetic field has a magnetic field strength that exceeds a saturation value of the coil element.

The thus externally applied magnetic field may particularly correspond to a relatively strong (i.e. above saturation value) direct current (DC) magnetic field is added to the externally applied magnetic or electromagnetic excitation field. The fact that the magnetic field strength exceeds a saturation value of the coil element means that the coil element will become saturated. In this context, the terms becoming saturated and/or saturation shall be understood as meaning that the inductance value of the coil for a very low current in the externally applied magnetic field, such as the saturating field, is reduced compared to the inductance value without such field. The inductance value in such cases may particularly be more than 5% lower, more particularly more than 10% lower, even more particularly more than 15% lower with the magnetic or saturating field applied compared to without such a field, i.e. the inductance may be less than 95% of its original value, more particularly less than 90% of its original value, even more particularly less than 85% of its original value when the coil is saturated.

As a result of this saturation, the efficiency of the coil element in responding to the externally applied magnetic or electromagnetic excitation field, and, hence, the efficiency of the sensing unit in transducing said magnetic or electromagnetic excitation field into an oscillation response, is affected, in particular reduced. This means that the absolute oscillation amplitude of the oscillation response will be reduced. As discussed herein above, the oscillation response is detected by a respective tracking array comprising a plurality of oscillation response detection units, such as a plurality of coils. Hereby, the amplitude is also detected by the oscillation response detection units.

For the gradient-based approach, the magnetic field causing the saturation may be provided with a gradient, i.e. may be provided such that the magnetic force exerted changes in quantity per unit distance. As indicated herein above, the magnetic field causing the saturation may be a saturating field that is provided in addition to the externally applied magnetic or electromagnetic excitation field.

Due to the saturating field having a gradient, the amplitude picked up by the position determination units in the tracking array will be different depending on the position and orientation at which the sensing unit is provided in the gradient field. Accordingly, the measured amplitude allows to restrict the position of the marker device to a certain area, such as a certain plane, in the excitation field—namely the one where the magnetic force exhibited by the magnetic field is such that the particular measured amplitude is obtained.

The measurement may then be repeated with the saturating field having a different gradient. Repeating this kind of measurement several times with different gradients allows to determine the specific position of the marker device.

Alternatively, in particular for saturation values below 10 µT, saturation may also/alternatively be achieved by the externally applied magnetic or electromagnetic excitation field. That is, no additional magnetic field may be necessary to saturate the coil element, but the coil element is saturated by the externally applied magnetic or electromagnetic excitation field. In these cases, the gradient-based approach may also be performed by provided the externally applied magnetic or electromagnetic excitation field with a gradient.

In these embodiments, the excitation in the marker device, i.e. the amplitude of the output voltage generated by the coil element and the amplitude of the mechanical oscillations performed by the resonator element correspond to a nonlinear function of the externally applied magnetic or electromagnetic excitation field. While the lack of an additional saturating field may mean that the oscillation response by the sensing unit may be weaker than expected according to a simple linear model, this still allows to determine the position and orientation of the marker device. The factor merely has to be included into the model used for determining the position.

The gradient-based position method has the benefit that it is even more accurate than the approach of performing position determination based on the different intensity values determined for the different oscillation response determination units when a saturation of the sensing unit, i.e. the coil element therein, is achieved at sufficient low excitation fields and strong enough gradients are used. As a further benefit, the frequencies that are involved in this kind of position determination are much lower, leading to less interference of non-ferromagnetic materials with the position determination process.

It is noted that, in some embodiments, further factors have to be considered. In some embodiments, the externally applied magnetic or electromagnetic excitation field comprises frequency components that are only half of the resonance frequency of the resonator element. In such cases, if no additional saturating field is provided, there is no excitation of the resonator element and, hence, the sensing unit will not provide an oscillation response. If, by contrast, a relatively small additional saturating field is provided, both, even and odd harmonics of the frequency components may be generated in the coil element. This results in a doubling of the frequency, which means that the output voltage provided to the resonator element can excite the resonator element to perform mechanical oscillations in resonant mode which, as discussed above, result in a piezoelectric voltage being provided to the coil element which, in turn, generates a magnetic field that can be detected by the tracking array. If, by further contrast, a relatively strong suturing field is applied, this may then reduce the excitation again, thereby leading to smaller oscillation responses to be detected until no oscillation response is detected anymore.

The phase of the oscillation response of the sensing unit may depend on the polarity of the saturating field. Accordingly, if the saturating field is provided with a gradient, different amplitudes and phases for the oscillation response, i.e. the magnetic field, may be determined. The changes may hereby depend very strongly on the position and the orientation of the sensing unit relative to the excitation field generator and the tracking array. Based on this understanding, the values of amplitude and phase may be computed for different positions in the gradient saturating field and for different gradient saturating fields, thereby allowing to determine the position and/or orientation very precisely.

The above half-frequency approach may also be performed with a one-third-frequency or with even lower frequencies. Instead of one coil, two or more coils may be used having different frequencies the sum of which and/or the harmonics of the sum correspond to the resonance frequency. These measures likewise allow to obtain a specific oscillation response profile for particular positions and orientations of the marker device. This effect may particularly be increased by applying a gradient saturation field.

Since each of the above possibilities to perform position tracking of the marker device have different capabilities depending on the position and orientation relative to the tracking array, in some embodiments, an optimization procedure is performed. This optimization procedure may start by specifying a sensitivity profile of the tracking array which allows to derive the position and orientation of the marker device. Further, a user input may be provided. The user input may encompass specifying that a resolution, typically along the direction more or less perpendicular to the rotation axis of the windings of the coil element, shall be maximized, while a repetition rate shall not be lower than a certain value. Based on these specifications, a computer may then be used to simulate or model all different constellations of excitation-amplitude, frequency and magnetic field. Based on this, the computer may determine with which constellation, the setting required by the user is best fulfilled for the given region of the marker.

It is noted that further boundary conditions such as the capabilities of the excitation field generator and/or the suturing field generator may be considered without increasing the complexity of the model. The modelling may be performed by using an optimization algorithm which is used to generate different parameter sets for different tracking situations which are then stored in a memory and retrieved when needed for a specific tracking procedure.

The gradient-based approach may also be used at the reception side, i.e. in the tracking system. That is, the tracking array, which typically comprises a plurality of magnetic coils as oscillation response detection units, may be used to generate a gradient when detecting or picking up the oscillation response. In case the sensing unit of the marker device is saturated, i.e. is provided at a position in the magnetic or electromagnetic field where the magnetic field strength exceeds the saturation value of the coil element, the oscillation response corresponds to a relatively small signal showing a slow decay over time. By contrast, in case the sensing unit of the marker device is not saturated, the oscillation response that may be detected has a larger signal strength, but exhibits a faster decay over time.

The sensing unit may further comprise a capacitive element.

The sensing unit may further be provided with a capacitive element, such as a capacitor. The capacitive element may particularly be added to the sensing unit such as to be connected in parallel to the coil element. That is, in a sensing unit comprising a capacitive element, the coil element and the resonator element may be connected in series and the capacitive element may be connected in parallel to the coil element. This essentially provides a resonator circuit which has an LC resonator and a piezoelectric resonator combined with one another.

The capacitive element may particularly be chosen to have a capacitance that amplifies the output voltage provided by the coil element in response to the externally applied magnetic or electromagnetic excitation field. This higher output voltage may then be provided to the resonator element, causing stronger deformations therein and, hence, a higher level of oscillation in the resonator element having piezoelectric properties for a given set of field parameters such as amplitude, frequency and duration. This, in turn, results in a higher piezoelectric voltage acting upon the coil element, meaning that the signal strength may be improved.

The value of the capacitance of the capacitive element may be chosen such that the resonance frequency of the coil element in the LC resonator corresponds to the resonance frequency of the resonator element, i.e. the piezoelectric resonator. This allows to reduce the amount of windings needed, as the loss during oscillation of the resonator circuit becomes low. With less windings, the manufacture of the marker device is simplified.

The coil element may further comprise at least one soft magnetic element.

In this context, the term soft magnetic may particularly be understood as referring to a material that is not permanently magnetized, i.e. no permanent magnet, but becomes magnetized in response to an external magnetic field. In absence of such a magnetic field, the magnetization of the soft magnetic material is very low.

In some embodiments, at least one soft magnetic element is provided at the coil element. In this context, the definition that the at least one soft magnetic element is provided at the coil element may particularly be understood as meaning that the at least one soft magnetic element may form a soft magnetic core of the coil element.

The at least one soft magnetic element may be provided in terms of a soft magnetic foil. The soft magnetic foil may be cut into respective soft magnetic stripes. The soft magnetic stripes may be placed in the coil element.

The at least one soft magnetic element may comprise a nickel iron alloy having a high nickel and a lower iron content, such as a nickel iron alloy with about 80% nickel and 20% iron, also known as permalloy. The at least one soft magnetic element may additionally or alternatively comprise a nanocrystalline soft magnetic alloy or an amorphous soft magnetic alloy. It is noted that an alloy chosen should be able to be provided with a sufficiently small thickness.

The soft magnetic element may be arranged in terms of stripes inside the coil element. Hereby, the soft magnetic element may particularly be inserted oblique to the magnetic axis of the coil element. This kind of arrangement may allow to determine the sixths degree of freedom for (i.e. the third angle) that is typically not available in position tracking if the sensing unit is excited at least twice with different levels of saturation by the magnetic field which may be the externally applied excitation field directly and/or an additional saturating field.

Alternatively or additionally, the sixth degree of freedom may be obtained by combining measurements with two marker devices having sensing units which oscillation response has different frequencies.

The at least one soft magnetic element may comprise a material having a demagnetizing factor resulting in a saturation at magnetic fields of strengths below 50 µT, in particular below 10 more particularly below 5 µT.

The at least one soft magnetic element may be selected to be of a material which has a low demagnetizing factor, i.e. provides for a small demagnetizing field. The demagnetizing factor may be low enough that the material of the at least one magnetic object is saturated at a few µT. The strength of the magnetic field at which the at least one magnetic object is saturated may be below 10 µT, more particular below 5 µT, even more particular below 2 µT. This has the benefit that saturation of the magnetic object is reached quickly, increasing the sensitivity of the resonator circuit.

The resonator element may comprise a crystalline material. The resonator element may have a resonance frequency below 300 kHz. The resonator element may comprise a main body and at least one prong attached thereto.

The resonator element may comprise or be made of a crystalline material. The crystalline material should hereby be chosen such as to have sufficient piezoelectric properties. The crystalline material may particularly comprise and/or correspond to a quartz crystal. Quartz is a well-known material for piezoelectric resonators and, hence, its resonance frequency is well-known. Accordingly, it is possible to provide a sensing unit comprising a resonator circuit comprising the coil element and the resonator element in which the components may easily be selected such as to provide an electrical field having a frequency that is close to or corresponds to the resonance frequency of the quartz crystal. This allows to obtain a high quality factor for the resonator circuit.

A further benefit of using quartz resides in the fact that quartz may be used in serial or parallel resonance as both eigenfrequencies are very close to each other and the resonance frequency thereof may even be slightly adjusted by respectively providing additional elements such as a trimmer in parallel or in series to the quartz crystal, depending on whether the quartz crystal is connected in parallel or in series. This even allows to compensate for manufacturing tolerances or the like. Further crystalline materials with similar properties may likewise be foreseen.

The resonator element may comprise a main body and at least one prong attached thereto. In particular, the resonator element may be of a fork type, in particular a tuning fork type, having two prongs attached to the main body. Providing the resonator element with the shape of a tuning fork may further improve the resonating properties and may also be beneficial in terms of using the marker device for sensing of physical properties, as outlined further below.

The sensing unit may further comprise a sensing material coupled to the resonator element. The sensing material may comprise a radiation-sensitive material, and/or a fluid-absorbing material.

The marker device may further be used for sensing at least one physical parameter of the surrounding environment of the marker device. In this context, the term physical parameter may be understood as referring to any parameter indicative of a surrounding environment of the marker device. The term physical parameter may particularly refer to a physically relevant value. The term physical parameter may, alternatively or additionally, refer to a chemically relevant value, i.e. a chemical parameter. The physical parameter may be indicative of radiation acting on the marker device. The physical parameter may be indicative of a humidity value in the surrounding environment. Further kinds of physical parameters that may be foreseen.

For the purpose of sensing the at least one physical parameter, the sensing unit may further comprise a sensing material that is coupled to the resonator element. The term coupled may hereby be understood as referring to a connection between the resonator element and the sensing material that results in a change of the oscillation frequency of the resonator element.

The sensing material may, for this purpose, particularly be arranged on the surface of the resonator element. The sensing material may be coupled to the sensing element in terms of being provided as a coating. The sensing material may be coupled to the resonator element in terms of a connecting element between the resonator element and the at least one soft magnetic element. Further methods of providing the coupling between the sensing material and the resonator element may be foreseen.

The sensing material may particularly correspond to a material that changes its mechanical properties due to the physical parameter it is intended to sense. Due to the sensing material being coupled to the resonator element, such a change in mechanical properties results in a change in the frequency of the resonator element and/or the quality factor of the marker device, both of which may be detected by a respective sensing unit in the tracking system, thereby allowing to detect the physical parameter.

In some embodiments, the marker device is supposed to also act as a radiation dosimeter. In this case, the sensing material provided may particularly be a radiation-sensitive material. Such radiation sensitivity may be achieved by providing a fluid material that solidifies in response to radiation.

Upon being irradiated, the fluid solidifies, leading to the previously moving—wobbling—droplets in the fluid being solidified and, hence, stopping movement. This causes a change in resonance frequency of the resonator element and, as such, of the marker device. Further, a change in quality factor of the marker device is likewise caused, thereby allowing to sense the presence of radiation.

In some embodiments, where the resonator element is of a tuning fork type, the fluid, i.e. the fluid droplets, may be placed at the tips of the fork. Upon solidification, the fluid expands, meaning the droplets of the fluid expand. At positions further away from the main body, the movement of the fork tips becomes faster due to this and the resonance frequency is decreased due do the increased moment of inertia.

The fluid material may also be used to connect the resonator element to the soft magnetic element. In some embodiments, where the resonator element is of a tuning fork type, in particular the prongs of the resonator element may be connected to the soft magnetic element via the fluid.

In some embodiments, the marker device is supposed to act as a moisture sensor. In this case, the sensing material should be sensitive to moisture. This moisture-sensitivity may be achieved by having the material being fluid-absorbing. In this case, when moisture is present, the material absorbs part of the moisture from the surrounding environment. This changes the mechanical properties of the material and, hence, affects the resonance frequency of the resonator element as described above.

The fluid-absorbing material may particularly be deposited on a surface of the resonator element. The fluid-absorbing material may be deposited in terms of a coating on the resonator element. In some embodiments, in which the resonator element is of the tuning fork type, the fluid-absorbing material may particularly be deposited on the surface of the prongs. The fluid-absorbing material may be deposited in terms of a coating on the prongs. Further manners of depositing may also be foreseen. The concept of depositing a fluid-absorbing material on the resonator element is based on the understanding that, in case the fluid-absorbing material absorbs part of the moisture, the effective mass of the resonator element on which the fluid-absorbing material is deposited is increased. This increase in effective mass results in an increase of the resonance frequency of the resonator element, which may then be picked up for the purpose of sensing.

The sensing unit may comprise an overvoltage protection. The term overvoltage protection is hereby to be understood as referring to a unit that protects the sensing unit from experiencing excessive voltage due to a very large externally applied magnetic or electromagnetic excitation field acting on the marker device and, hence, the sensing unit, due to a marker device being too close to the excitation field generator.

More than one marker device might have to be tracked. That is, a plurality of marker devices may be tracked at once. In such cases, it might be difficult to coordinate that the externally applied magnetic or electromagnetic field is only provided when all marker devices are far away enough from the excitation field generator to not experience an excessive field which may lead to the coil element of the sensing unit generating an excessive voltage that might destroy the resonator element. For those cases, an overvoltage protection may be provided. The overvoltage protection may particularly be provided in terms of a circuit comprising two antiparallel diodes, such as Zener diodes, connected in series which are then connected in parallel to the coil element. Hereby, a breakdown voltage of the diodes should be provided at a value below a parameter value for a voltage at which the resonator element, or any other component in the resonator circuit having an even lower voltage rating, would be destroyed.

According to a further aspect, a tracking system for tracking a marker device as described above is provided. The tracking system comprises an excitation field generator for generating a magnetic or electromagnetic acting on a sensing unit of the marker device, a tracking array for detecting a magnetic field of the sensing unit and for generating one or more response signals based on the magnetic field, and a position determination unit for determining the position of the marker device based on the one or more response signals. The tracking system may further comprise a physical parameter determination unit for determining a physical parameter based on the one or more response signals. The tracking system may further comprise a saturating field generator for generating a saturating magnetic field having a magnetic field strength set such that the coil element and/or the soft magnetic element reach saturation. In some embodiments, the excitation field generator and/or the saturation field generator and/or the tracking array are configured to generate a gradient field.

According to a further aspect, a tracking system is provided. The tracking system may comprise an excitation field generator. The excitation field generator may particularly correspond to a magnetic or electromagnetic field generator comprising a plurality of magnetic coils, in particular a coil array. That is, the excitation field may be a magnetic or electromagnetic excitation field. The excitation field is used to induce oscillations in the sensing unit as described above.

These oscillations result in an oscillation response of the sensing unit being detectable. For this purpose, the tracking system comprises a respective tracking array capable of detecting the oscillation response. Hereby, the tracking array may particularly be provided by the same plurality of coils as the excitation field generator. That is, the excitation field generator may also serve as the tracking array, i.e. the detector of the magnetic field generated by the resonator circuit in the system. The tracking array may also be provided as a separate unit, i.e. in terms of a second plurality of magnetic coils, in particular a second coil array.

The tracking array is hereby configured to detect the magnetic field provided by the sensing unit and to generate a respective response signal on the basis of this detection. The tracking array may particularly comprise a plurality of oscillation response detection units which may be provided in terms of magnetic coils. These oscillation response detection units may be arranged in a particular geometrical arrangement, such as a coil array. Due to the geometrical arrangement of the plurality of oscillation response detection units, the oscillation response that is picked up by the individual oscillation response detection units may be dependent on the distance and orientation of the marker device relative to the respective oscillation response detection unit, meaning that each oscillation response detection unit may obtain a different value for the oscillation response to be included in the response signal.

The response signal is then provided to a respective position determination unit. The position determination unit is configured to use the response signal to determine the position of the marker device on the basis of the response signal. This position determination is based on the assumption that an oscillation response as obtained by a specific oscillation response detection unit in the tracking array is dependent on the position and orientation of the marker device in the externally applied magnetic or electromagnetic excitation field and the distance and orientation relative to the specific oscillation response detection unit. The position determination unit hereby essentially compares modelled response signals for a plurality of different positions and orientations of the marker device against the obtained response signal and selects the closest match. Based on this matching, the position determination unit determines the position of the marker device.

The tracking system may also perform the gradient-based approach as discussed herein above. The saturation of the coil element and/or the soft magnetic element may hereby be achieved by the externally applied excitation field directly. Alternatively, the saturation may be achieved by a saturating field. In order to generate this saturating field, the tracking system may comprise a saturating field generator. The saturating field generator may correspond to the excitation field generator for generating the magnetic or electromagnetic excitation field. The saturating field generator may be a separate element.

That is, the externally applied magnetic or electromagnetic excitation field and/or the saturating field may have a magnetic field strength that exceeds a saturation value of the coil element and/or the soft magnetic element, leading to a saturation of the coil element and a respective reduction in efficiency in responding to the externally applied magnetic or electromagnetic excitation field. As a result the absolute oscillation amplitude of the magnetic field is reduced.

For performing the gradient-based approach, the externally applied magnetic or electromagnetic excitation field and/or the saturating field may correspond to a gradient field. Due to the externally applied magnetic or electromagnetic field being a gradient field, the amplitude of the oscillation response, i.e. the magnetic field, that is detected by the tracking array will be different depending on the position at which the sensing unit is provided in the gradient field, allowing to restrict the position of the marker device. The tracking system may then be used to repeat the measurement for several gradients. This allows to determine the position of the marker device with high accuracy as described above.

The tracking system may be configured to use the gradient-based approach also at the tracking array side. That is, the tracking array may be used to generate a gradient when detecting or picking up the magnetic field generated by the sensing unit. In case the sensing unit of the marker device is saturated, the magnetic field picked up by the tracking array will be relatively small and showing a slow decay over time. By contrast, in case the sensing unit of the marker device is not saturated, the magnetic field that is picked up by the tracking array is large and exhibits a fast decay over time. This may be beneficial to further enhance accuracy.

The tracking system may further comprise a physical parameter determination unit for determining a physical parameter based on the one or more response signals. In these cases, the sensing unit preferably comprises a sensing material. As described above, the sensing material changes the frequency with which the resonator element oscillates when the physical parameter for which it is sensitive is present. This change in frequency affects the magnetic field generated by the coil element and is thus appreciable in the oscillation response picked up by the tracking array. Accordingly, the response signal generated by the response detection unit will also be indicative of this change in frequency. The physical parameter determination unit may then process the response signal to provide further information about the physical parameter having been sensed. The value of the physical parameter may hereby be determined by the physical parameter determination unit.

According to yet another aspect, a method for tracking a marker device as described above is provided, comprising the steps of generating a magnetic or electromagnetic excitation field acting on a sensing unit of the marker device, detecting an oscillation response of the sensing unit, generating one or more response signals based on the oscillation response, and determining the position of the marker device based on the one or more response signals.

In an even further aspect, a computer program for controlling a tracking system as described above to track a marker device as likewise described above is provided, which, when executed by a processing device, is adapted to perform the method as described above. In a further aspect, a computer-readable medium having stored thereon the computer program is provided. The computer-readable medium could be e.g. a non-transitory computer readable medium.

It shall be understood that the marker device of claim 1, the tracking system of claim 9, the method of claim 13, the computer program of claim 14, and the computer-readable medium of claim 15, have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter. The invention is defined by the independent claims. The dependent claims define advantageous embodiments.

DETAILED DESCRIPTION OF EMBODIMENTS

Figure 1A:
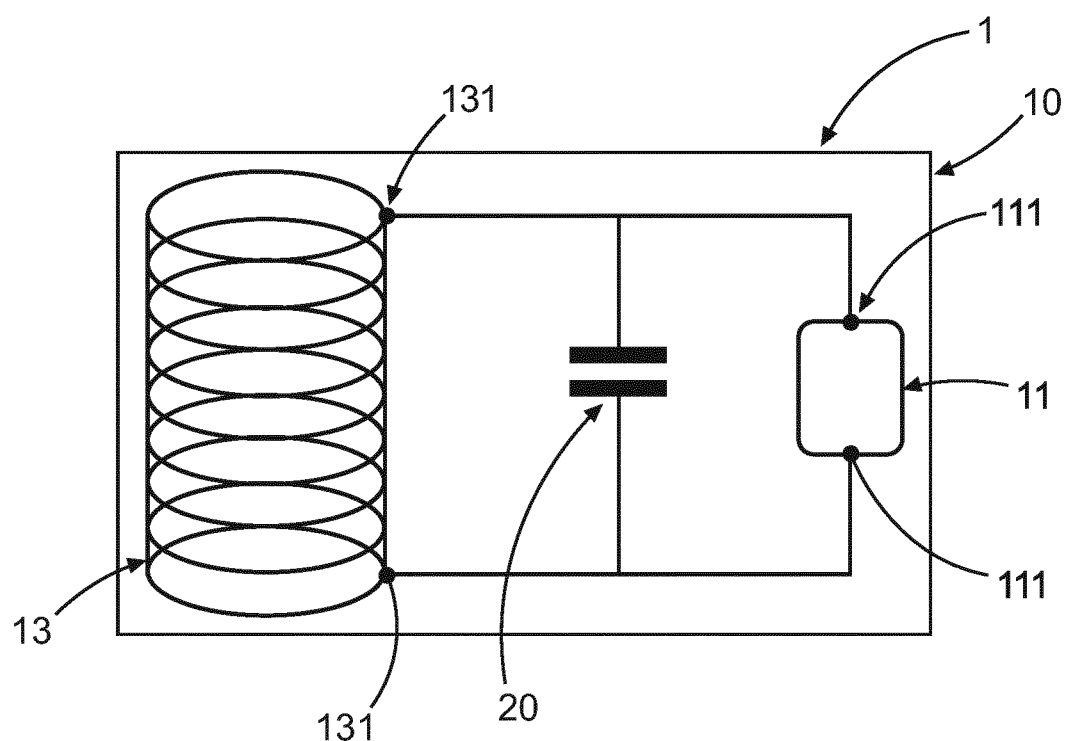
FIG. 1A shows schematically and exemplarily a sensing unit according to a first embodiment.

FIG. 1A schematically and exemplarily shows an embodiment of a marker device 1 for being attached to a device, in particular a medical device, for being tracked by a tracking system, for example during a procedure, such an invasive procedure, performed on a patient. The marker device 1 comprises a sensing unit 10 according to a first exemplary embodiment. The sensing unit 10 comprises, in the specific embodiment according to FIG. 1A, a resonator element 11, a coil element 13 and a capacitive element 20. The resonator element 11 and the coil element 13 are hereby connected with each other in series. Further, the capacitive element 20 is connected in parallel to the coil element.

The marker device 1 may be used for tracking a device to which the marker device 1 is attached using a respective tracking system. For this purpose, an excitation field generator may be provided to generate an externally applied magnetic or electromagnetic excitation field having particular frequency components. This magnetic or electromagnetic excitation field acts on the coil element 13. In the specific embodiment according to FIG. 1, further a saturating field, in particular a DC magnetic field, is generated by the excitation field generator having a strength that results in a saturation of the coil element 13.

The coil element 13 transduces the magnetic or electromagnetic excitation field into a respective output voltage having a particular frequency which is close to the resonance frequency of the resonator element 11. Hereby, due to the saturation of the coil element 13 by the DC magnetic field the efficiency of this transducing is reduced and the output voltage is rather small.

The output voltage is then provided, via terminals 131 of the coil element to the terminals 111 of the resonator element 11 via a respective electrical connection. The output voltage is thus fed to the resonator element 11 via terminals 111. Hereby, output voltage is, prior to being fed to the resonator element 11, amplified by the capacitive element 20. That is, capacitive element 20 is provided to have a capacitance that allows amplification of the output voltage provided by the coil element 13 to resonator element 11. The output voltage is then received by the resonator element 11 and effects a deformation therein.

In the specific embodiment of FIG. 1A, the resonator element 11 corresponds to a piezoelectric crystal. In response to receiving the adjusted output voltage from the coil element 13, the resonator element 11 is deformed. Due to the frequency component being within a resonant frequency of the resonator element 11, the deformation is excited in the resonant mode. As such, the resonator element 11 starts performing mechanical oscillations in a resonant mode, leading to the oscillations being persistent for a while, even if no output voltage is provided from the coil.

The deforming of the resonator element 11 hereby leads to a voltage being generated by the resonator element 11 due to its piezoelectric properties. The generated voltage, called piezoelectric voltage in the following, is then provided to the coil element 13, resulting in a current being generated through the coil element 13. This current causes the generation of a magnetic field in the coil element 13. This resulting magnetic field may then be detected by the tracking system and used for position determination and/or sensing as described further below. Now, due to the oscillations being persistent, even without the resonator element 11 receiving the output voltage, the resonator element 11 acts as an energy storage, continuing providing the piezoelectric voltage to the coil element 13. This leads to the current being continuously generated through the coil element 13, meaning that the coil element 13 continues providing a magnetic field that may be detected by the tracking array. Accordingly, by using the resonator element 11 as an energy storage, the damping of the resonant circuit formed by the resonator element 11, the capacitive element 20 and the coil element 13 may be educed, meaning that the circuit has a high quality factor.

Figure 1B:
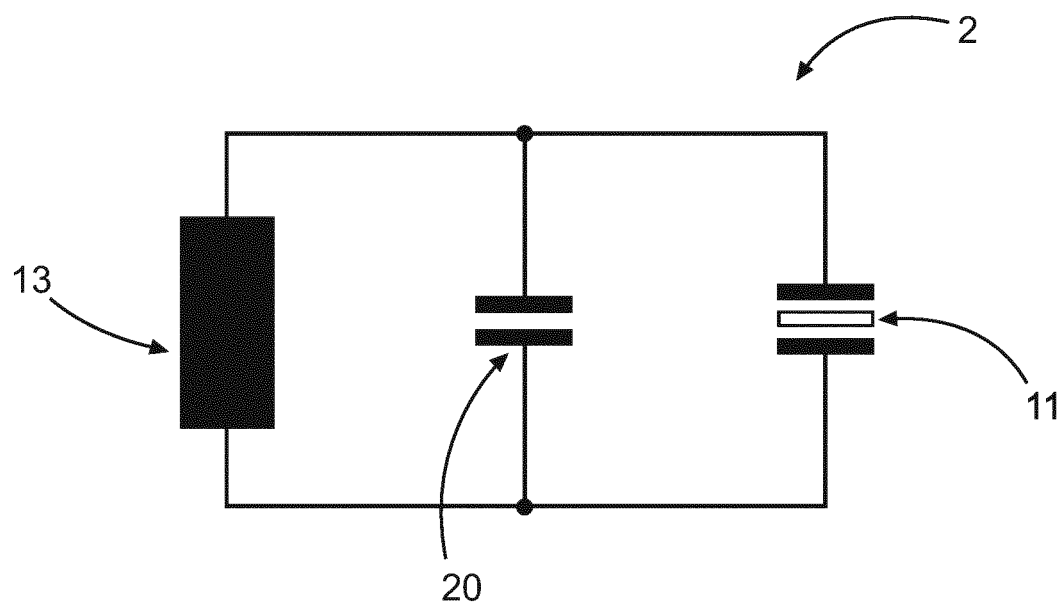
FIG. 1B shows schematically and exemplarily a resonant circuit representative of the sensing unit according to the first embodiment.

FIG. 1B schematically and exemplarily shows a circuit diagram 2 representative of the resonant circuit formed by the resonator element 11, the coil element 13 and the capacitive element 20. As shown in the circuit diagram, the resonator element 11 and the coil element 13 are connected in series and the capacitive element 20 is connected in parallel to the coil element 13.

Figure 2A:
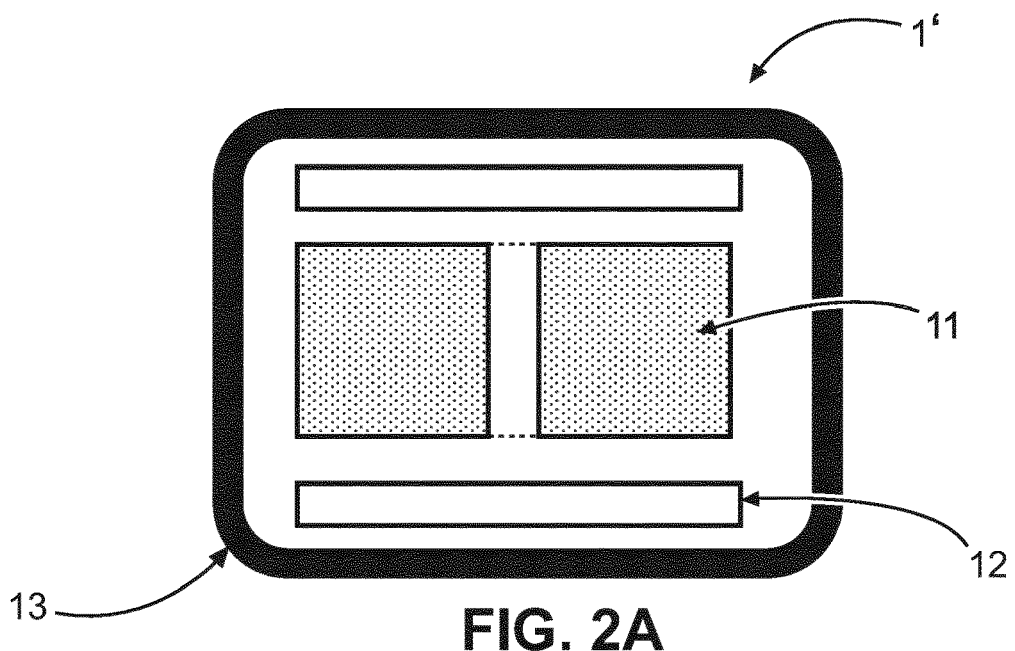
FIG. 2A shows schematically and exemplarily a sensing unit according to a second embodiment in a front view.
Figure 2B:
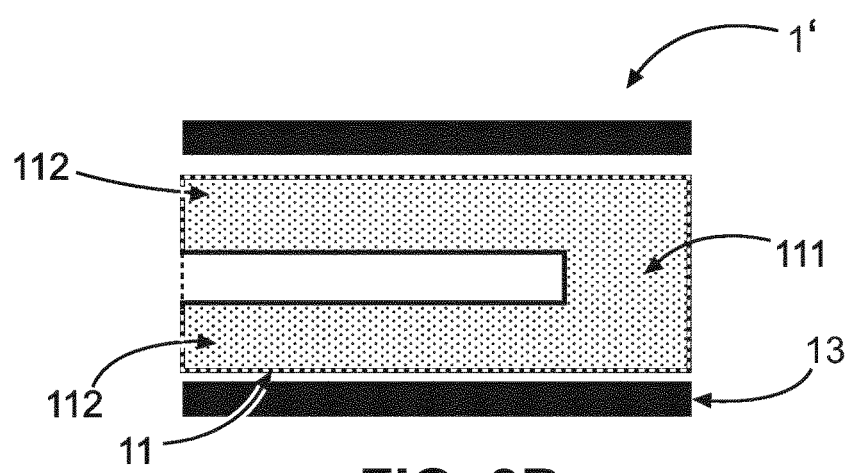
FIG. 2B shows schematically and exemplarily the sensing unit according to the second embodiment in a side view.
Figure 2C:
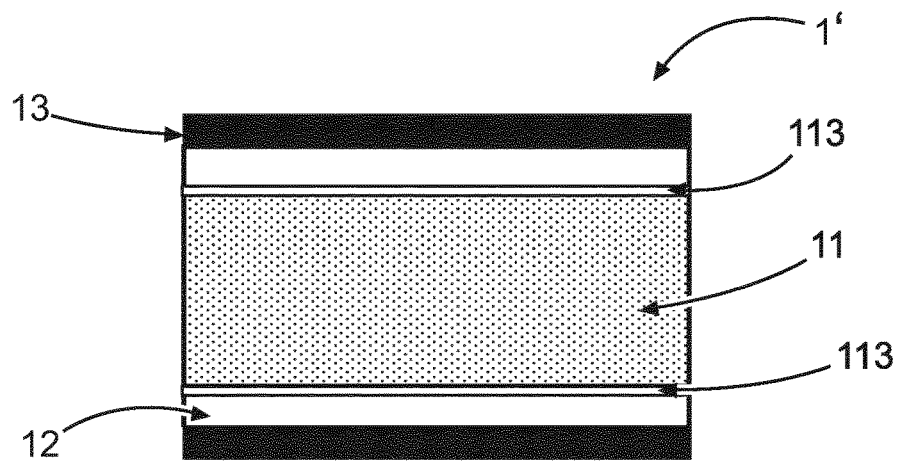
FIG. 2C shows schematically and exemplarily the sensing unit according to the second embodiment in a top view.

Referring now to FIGS. 2A to 2C, these figures show a marker device 1', including a sensing unit 10 according to a second embodiment in a front view, a side view and a top view, respectively. The arrangement shown in FIGS. 2A to 2C is particularly beneficial for marker devices 1' for which space may be an issue, i.e. for marker devices 1' that should be appropriately small.

In the specific embodiment according to FIG. 2A, the sensing unit 10 comprises a resonator element 11, a soft magnetic element 12, and a coil element 13. The marker device 1' further comprises a sensing material (not shown in FIG. 2A) that is provided to connect the resonator element 11 and at least one of the soft magnetic elements 12.

The resonator element 11 of sensing unit 10 has piezoelectric properties. That is, the resonator element 11 is made of or comprises a material having piezoelectric properties. In the specific embodiment according to FIGS. 2A to 2C, the resonator element 11 comprises a quartz crystal. Quartz is a material well known for its piezoelectric properties.

In the specific embodiment of FIGS. 2A to 2C, the soft magnetic elements 12 are provided in terms of two magnetic stripes 12 which have been formed from a magnetic foil. The two magnetic stripes 12 are arranged in the coil element 13, such as to form a soft magnetic core of the coil element 13. In the specific embodiment of FIGS. 2A to 2C, the soft magnetic elements 12 are made of a material which has a demagnetizing factor such that a saturation of the magnetic objects 12 is achieved a few μT, in particular at below 50 μT, more particularly below 10 μT, even more particularly below 5 μT. In the specific embodiment according to FIGS. 2A to 2C, the soft magnetic element may, for this purpose, be made of a nickel-iron alloy having a high amount of nickel, such as permalloy.

The sensing unit 10 of marker device 1 in the exemplary embodiment of FIGS. 2A to 2C further comprises a coil element 13. In the specific embodiment according to FIGS. 2A to 2C, the coil element 13 particularly corresponds to a winding that is wound around the resonator element 11 and in which the soft magnetic elements 12 are arranged. Hereby, the winding is wound around the resonator element 11 in order to achieve some distance between the axis around which the winding 13 is provided in order to improve efficiency. In order to obtain sufficient efficiency while at the same time allowing for the coil element 13 to be easily saturated, the coil element 13 should be provided of a suitable material. In the specific embodiment according to FIGS. 2A to 2C, the winding of the coil element 13 is made of copper.

In FIG. 2A, the marker device 1 comprising the sensing unit 10 has been schematically and exemplarily shown in a front view. Further illustrations of the geometrical arrangement of the resonator element 11, the soft magnetic element 12 and the coil element 13 of sensing unit 10 may be appreciated from FIGS. 2B and 2C.

Accordingly, as shown in FIG. 2B, the resonator element 11 has a tuning fork type shape comprising a main body 111 made of the quartz crystal and prongs 112 which may also be made of quartz or may be made of a different material. Hereby, the prongs 112 are provided such that something, e.g. a coating or the like, may be added to them in order to modify the resonant frequency and/or the quality factor, whereas the main body 111 is not modified. The benefit of this tuning fork type shape of the resonator element 11 resides in an improvement of the oscillation properties of the resonator element 11.

In the specific embodiment according to FIGS. 2A, 2B and 2C, the marker device 1' is further configured to act as a radiation dosimeter. As shown in FIG. 2C, for this purpose, a radiation-sensitive material 113 is provided to connect the resonator element 11 and the soft magnetic elements 12, i.e. the soft magnetic stripes, with one another. The radiation-sensitive material 113 in the specific embodiment according to FIGS. 2A, 2B and 2C corresponds to a fluid that solidifies under radiation. That is, when the sensing unit 10 is exposed to radiation, the radiation-sensitive material 113 changes from a fluid state to a solid state. This change in state affects the mechanical properties of the resonator element 11 and, hence, the frequency with which the resonator element 11 oscillates. This change in frequency may also be detected by the tracking system and used, by a respective physical parameter determination unit, to sense the presence of radiation.

Figure 3:
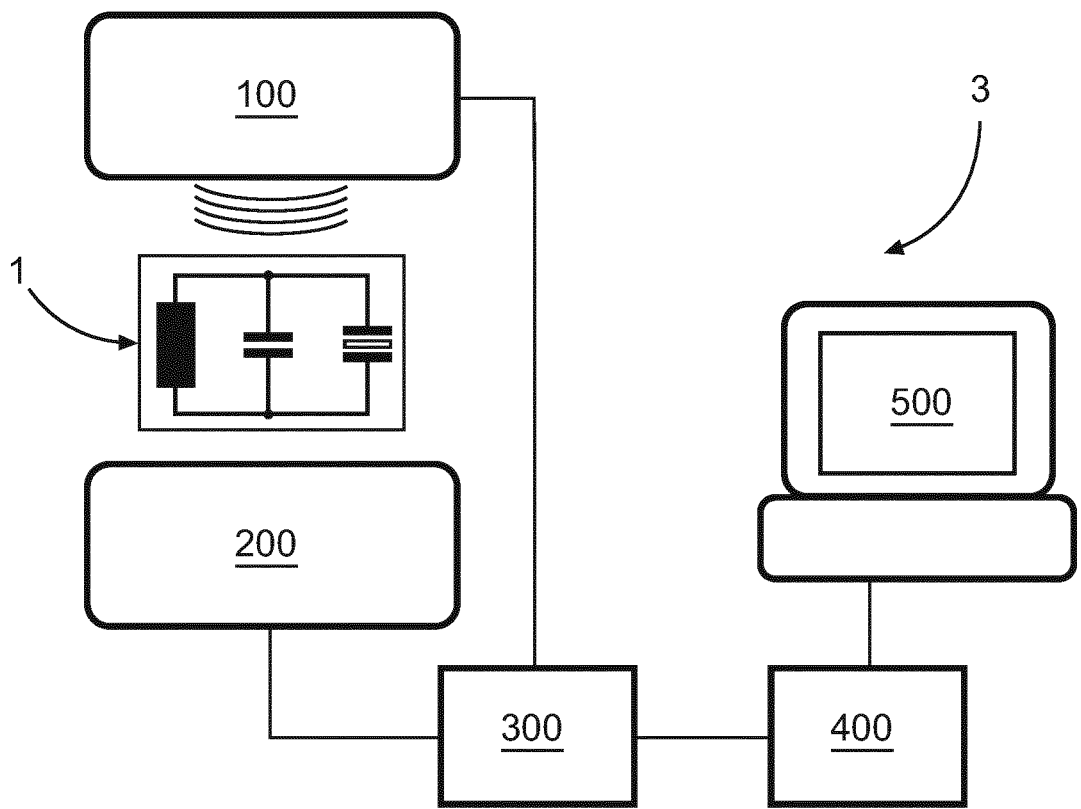
FIG. 3 shows schematically and exemplarily an embodiment of a tracking system for tracking the marker device according to a first embodiment.

FIG. 3 schematically and exemplary shows an embodiment of a tracking system 3. The tracking system 3 comprises an excitation field generator 100 for generating an external magnetic or electromagnetic excitation field along with a saturating field and a tracking array 200 for detecting the oscillation response of the sensing unit 10 in the marker device 1 in terms of the magnetic field of the marker device 1 and for generating one or more response signals based on the oscillation response. Further, the tracking system 3 comprises a position determination unit 300 for determining the position of the marker device 1 based on the one or more response signals and a physical parameter determination unit 400 for determining a physical parameter based on the one or more response signals. That is, in the embodiment according to FIG. 3, the excitation field generator and the saturating field generator are provided by the same unit 100, whereas the tracking array 200 is provided by a different unit. However, the excitation field generator and the saturating field generator may be separate units. The excitation field generator, the saturating field generator and the tracking array may be provided as one unit, as exemplarily shown in FIG. 4 as discussed further below. The excitation field generator and the tracking array may be provided as a single unit, whereas the saturating field generator is provided as a different unit. The saturating field generator and the tracking array may correspond to the same unit, with the excitation field generator being provided as a different, separate unit.

In the embodiment according to FIG. 3, the excitation field generator 100 generates an external excitation field, which, in the embodiment according to FIG. 3, corresponds to an electromagnetic excitation field. The external excitation field causes an oscillation response to be generated by the sensing unit 10 in the marker device 1 as described above in relation to FIGS. 1A to 2C.

That is, the externally applied electromagnetic excitation field results in the coil element 13 being affected by the electromagnetic excitation field. This results in an output voltage of the coil element 13 being generated. This output voltage hereby provides a frequency component that is close to the resonant frequency of the resonator element 11. This may be achieved by selecting the coil element 13, respectively its materials and winding, appropriately and/or by selecting the electromagnetic field appropriately and/or by using a capacitor that adjusts the frequency to be close to the resonant frequency.

The output voltage is then provided to the resonator element 11. In response to the output voltage received, the resonator element 11 is deformed due to its piezoelectric properties. This causes the performance of mechanical oscillations in a resonant mode due to the frequency components of the output voltage. This, in turn means, that the mechanical oscillations are persistent, even when the externally applied excitation field is switched off. The mechanical oscillations cause a generation of a piezoelectric voltage which is then provided back to the coil element 13. This causes a current being generated in the coil element 13, resulting in a magnetic field being emitted by the coil element 13. Since the mechanical oscillations are persistent due to being excited in resonant mode, the damping of the resonant circuit is low, due to the energy-storing properties of the resonator element. Hence, the thus created resonant circuit has a high quality factor and, therefore, high frequency resolution, and high sensitivity. Further, it may be read out in a rather simple manner, due to the high quality factor. In the exemplary embodiment according to FIG. 3, the marker device 1 further comprises a sensing material that is coupled to the resonator element 11. In the specific embodiment according to FIG. 3, the sensing material is a radiation-sensitive material provided as a connecting material between the resonator element 11 and the magnetic objects 12. Hereby, the sensing material corresponds to a fluid that solidifies upon being subjected to radiation. In the specific embodiment according to FIG. 3, when the marker device 1 experiences radiation, the fluid sensing material becomes solid. This causes a change in the oscillation frequency of the resonator element 11, which, in turn, changes the piezoelectric voltage output by the resonator element 11 and the magnetic field generated by the coil element 13 in response thereto. Hence, the change affects the oscillation response of the entire resonant circuit.

This oscillation response by the resonant circuit may be picked up by the tracking array 200. The tracking array 200 uses the oscillation response to generate a response signal. The response signal is provided, from the tracking array 200 to the position determination unit 300. The position determination unit 300 receives the response signal from the tracking array 200 and, further, receives position information from the excitation field generator 100. Based on the position information from the excitation field generator 100 and the response signal from the tracking array 200, the position determination unit 300 may determine the position of the marker device 1 and, hence, of the device to which the marker device is attached, relative to the excitation field generator 100 and the tracking array 200. This allows the position detection unit 300 to determine the position of the marker device 1.

In particular, for position tracking, the specific embodiment according to FIG. 3 foresees using a gradient-based tracking approach employing saturation of the coil element 13 in the marker device 1. That is, a saturating field generator 100 is provided for generating an external saturating field which causes the coil element 13 to be saturated. Hereby, this saturating field is provided with a gradient.

This gradient means that the amplitude picked up by the tracking array 200 will be different depending on the position and orientation at which the sensing unit is provided in the gradient field. Accordingly, the measured amplitude allows to restrict the position of the marker device 1 to a certain area, such as a certain plane, in the excitation field by correlating the position information provided from the excitation field generator 100 and the tracking array 200.

This measurement may then be repeated with the saturating field having a different gradient. Repeating this kind of measurement several times with different gradients allows to determine the specific position of the marker device. The specific position of the marker device may then be output for the user on display unit 500.

Although, in the specific embodiment according to FIG. 3, an additional saturating field is generated and used, in other embodiments, the externally applied excitation field may be used to saturate the coil element 13 directly. In these embodiments, the excitation in the marker device 1, i.e. the amplitude of the output voltage generated by the coil element 13 and the amplitude of the mechanical oscillations performed by the resonator element 11 correspond to a non-linear function of the externally applied excitation field.

The tracking system 3 further comprises a physical parameter determination unit 400. The physical parameter determination unit 400 also receives the response signal from the tracking array 200. The response signal, being based on the oscillation response by the tracking array 10, contains information about the change in frequency caused by the solidifying of the fluid connection material between the resonator element 11 and the magnetic objects 12. Based on this information about the change in frequency, the physical parameter determination unit 400 may thus determine the presence of radiation that has acted on the marker device 1.

This sensing information may then also be provided to display unit 500, which is configured to generate a graphical representation of the tracking and sensing and output this graphical representation to a user.

Using this arrangement, it is possible to provide a tracking and sensing system having a high frequency resolution and a high quality factor for both, small and large dimensions, i.e. independent of the dimensioning of the devices.

Figure 4:
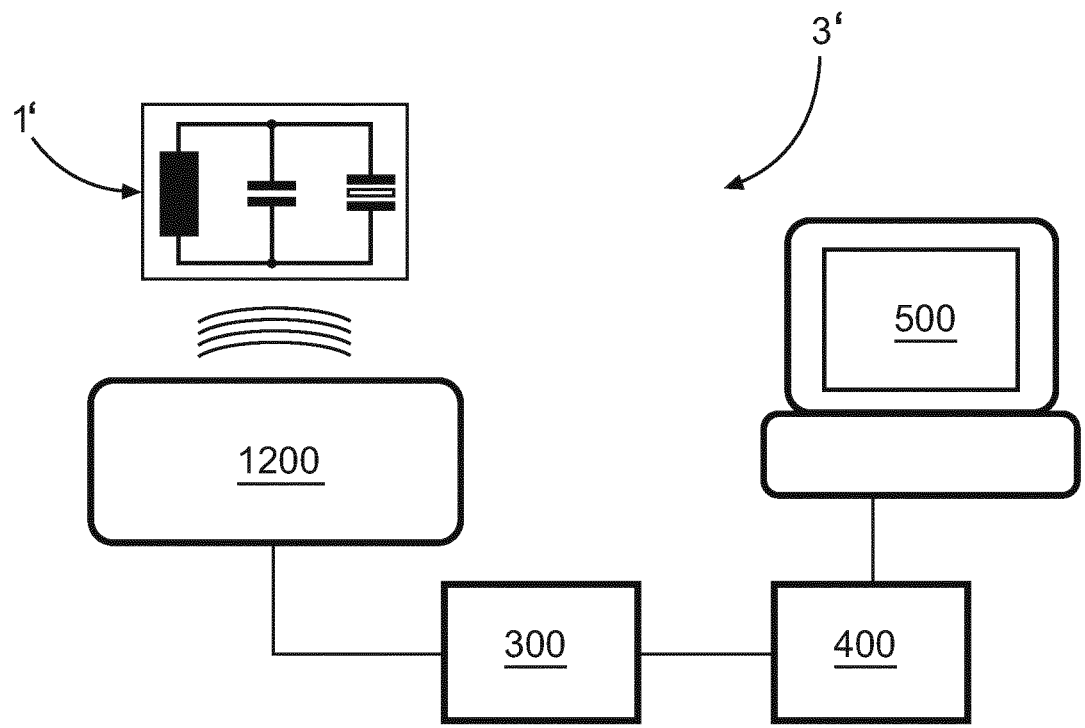
FIG. 4 shows schematically and exemplarily an embodiment of a tracking system for tracking the marker device according to a second embodiment.

To that end, FIG. 4 schematically and exemplary shows a second embodiment of a tracking system 3'. In general, the second embodiment according to FIG. 4 works in the same fashion as the embodiment according to FIG. 3. Insofar it shall be referred to FIG. 3 for sake of brevity.

The difference between the embodiment of FIG. 4 and the embodiment of FIG. 3 as discussed above, resides in the fact that, in the embodiment according to FIG. 4, the excitation and saturating field generator 100 and the tracking array 200 are provided as a single magnetic array 1200. That is, in the embodiment according to FIG. 4, the same magnetic array that is used to generate the excitation field and/or the saturating field is also used for picking up the oscillation response by the marker device 1. For this purpose, the magnetic array 1200 comprises a circuit that allows to switch between a transmission mode, in which the excitation field and/or the saturating field is generated and provided to act on the marker device 1 and a reception mode, in which the magnetic field generated by the coil element 13 in the marker device 1 may be picked up. Due to the resonant circuit in the marker device 1 having a high quality factor, this switching may be relatively slow. #As stated, the response generation by the sensing unit 10 in the marker device 1 and the processing of the response signals in the position determination unit 300, the physical parameter determination unit 400 and the display unit 500 are the same as described in relation to FIG. 3, only that there is no communication between two separate units, i.e. the excitation and saturating field generator 100 and the tracking array 200 necessary, as the magnetic array 1200 already is aware of the values and positioning of the excitation field and/or the saturating field generated.

Accordingly, the embodiment according to FIG. 4, a rather simply tracking system 3' may be provided in which fewer components are used.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Procedures like the processing of the oscillation response, the generating of the response signals, the determining of the position of the marker device and/or the sensing of a physical parameter based on the response signal, et cetera, performed by one or several units or devices can be performed by any other number of units or devices. These procedures, particularly the tracking of the marker device as performed by the tracking system in accordance with the method for tracking the marker device, can be implemented as program code of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

A marker device to be tracked and a respective tracking system are provided which make use of a sensing unit comprising a resonator element with piezoelectric properties and a coil element, whereby an externally applied excitation field having a particular frequency is applied to act on the sensing unit and wherein the sensing unit responds to the externally applied excitation field by the resonator element performing persisting mechanical oscillations in resonant mode, the persisting mechanical oscillations resulting in a piezoelectric voltage causing the coil element generating a magnetic field that may then be detected by the tracking system and used for determining the position of the marker device and/or sensing a physical property in the surrounding environment of the marker device.

The invention claimed is:

1. A passive marker device that comprises:
   a sensor comprising a resonator having piezoelectric properties, and a coil;
   wherein the coil provides to the resonator an output voltage in response to an external excitation field,
   wherein the resonator transduces the output voltage into respective mechanical oscillations in a resonant mode and provides a piezoelectric voltage to the coil, and
   wherein the coil transduces the piezoelectric voltage into a magnetic field.

2. The marker device according to claim 1, wherein the sensor further comprises a capacitor.

3. The marker device according to claim 1, wherein the coil further comprises at least one soft magnet.

4. The marker device according to claim 3, wherein the at least one soft magnet comprises a material having a demagnetizing factor resulting in a saturation at fields of strengths below 50 µT, in particular below 10 µT, more particularly below 5 µT.

5. The marker device according to claim 1, wherein the resonator comprises a crystalline material.

6. The marker device according to claim 1, wherein the sensor further comprises a sensing material coupled to the resonator.

7. The marker device according to claim 6, wherein the sensing material comprises a radiation-sensitive material or a fluid-absorbing material.

8. The marker device according to claim 1, wherein the sensor further comprises an overvoltage protection.

9. A tracking system for tracking a marker device according to claim 1, the tracking system comprising:
   an excitation field generator for generating a magnetic or electromagnetic excitation field;
   a tracking array for detecting a field from the marker device and for generating one or more response signals based on the field; and a position determinator for determining a position of the marker-device based on the one or more response signals.

10. The tracking system according to claim 9, further comprising a physical parameter determinator for determining a physical parameter based on the one or more response signals.

11. The tracking system according to claim 9, further comprising a saturating field generator for generating a saturating field having a field strength set such that the coil reaches saturation.

12. The tracking system according to claim 11, wherein the excitation field generator and/or the saturating field generator and/or the tracking array is or includes a gradient field generator.

13. A method for tracking a marker device according to claim 1, the method comprising the steps of:
generating an excitation field,
detecting a field of the marker device,
generating one or more response signals based on the field, and
determining the position of the marker device based on the one or more response signals.

14. A non-transitory computer-readable medium having stored thereon a computer program for controlling a tracking system to track a marker device that, when the computer program is executed by a processor, causes the tracking system to perform the method according to claim 13.

15. The marker device according to claim 6, wherein the sensing material comprises a radiation-sensitive material and a fluid-absorbing material.

* * * * *